United States Patent [19]
Samuels

[11] Patent Number: 6,007,575
[45] Date of Patent: Dec. 28, 1999

[54] INFLATABLE INTRALUMINAL STENT AND METHOD FOR AFFIXING SAME WITHIN THE HUMAN BODY

[76] Inventor: Shaun Laurence Wilkie Samuels, 1055 Sonoma Ave., Menlo Park, Calif. 94025

[21] Appl. No.: 08/870,745

[22] Filed: Jun. 6, 1997

[51] Int. Cl.⁶ .............................. A61F 2/02; A61F 2/04; A61F 2/06; A61M 39/00
[52] U.S. Cl. .................................. 623/1; 623/11; 623/12; 606/192; 606/194; 606/195; 606/198
[58] Field of Search .................................. 623/1, 12, 11; 606/192, 194, 195, 198

[56] References Cited

U.S. PATENT DOCUMENTS

| | | | |
|---|---|---|---|
| 5,156,620 | 10/1992 | Pigott | 623/1 |
| 5,370,691 | 12/1994 | Samson | 623/12 |
| 5,494,029 | 2/1996 | Lane et al. | 128/207.15 |
| 5,554,180 | 9/1996 | Turk | 623/1 |
| 5,554,185 | 9/1996 | Block et al. | 623/2 |
| 5,649,978 | 7/1997 | Samson | 623/12 |

*Primary Examiner*—Paul B. Prebilic
*Assistant Examiner*—Choon P. Koh
*Attorney, Agent, or Firm*—Rudnick & Wolfe

[57] ABSTRACT

An inflatable intraluminal stent for attachment to the interior surface of a tubular structure within the human body is disclosed. The stent features a cuff having an inflatable chamber and a friction-enhancing outer surface. The friction-enhancing outer surface engages the interior surface of the tubular structure without penetration when the inflatable cuff is in an inflated condition. An intraluminal medical device may be attached to the inner surface of the stent. A valve is integral with the inflatable cuff and allows for the inflation, deflation and sealing of the inflatable cuff.

24 Claims, 10 Drawing Sheets

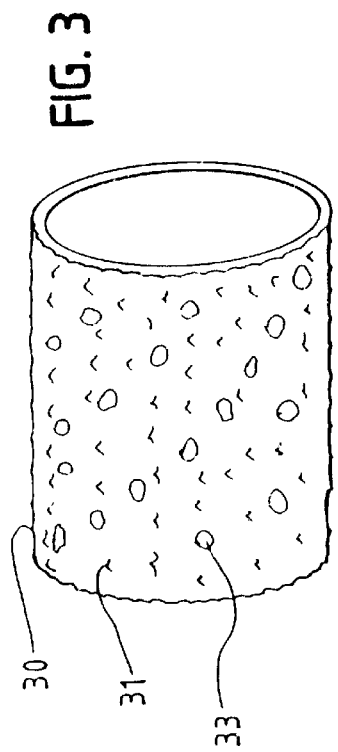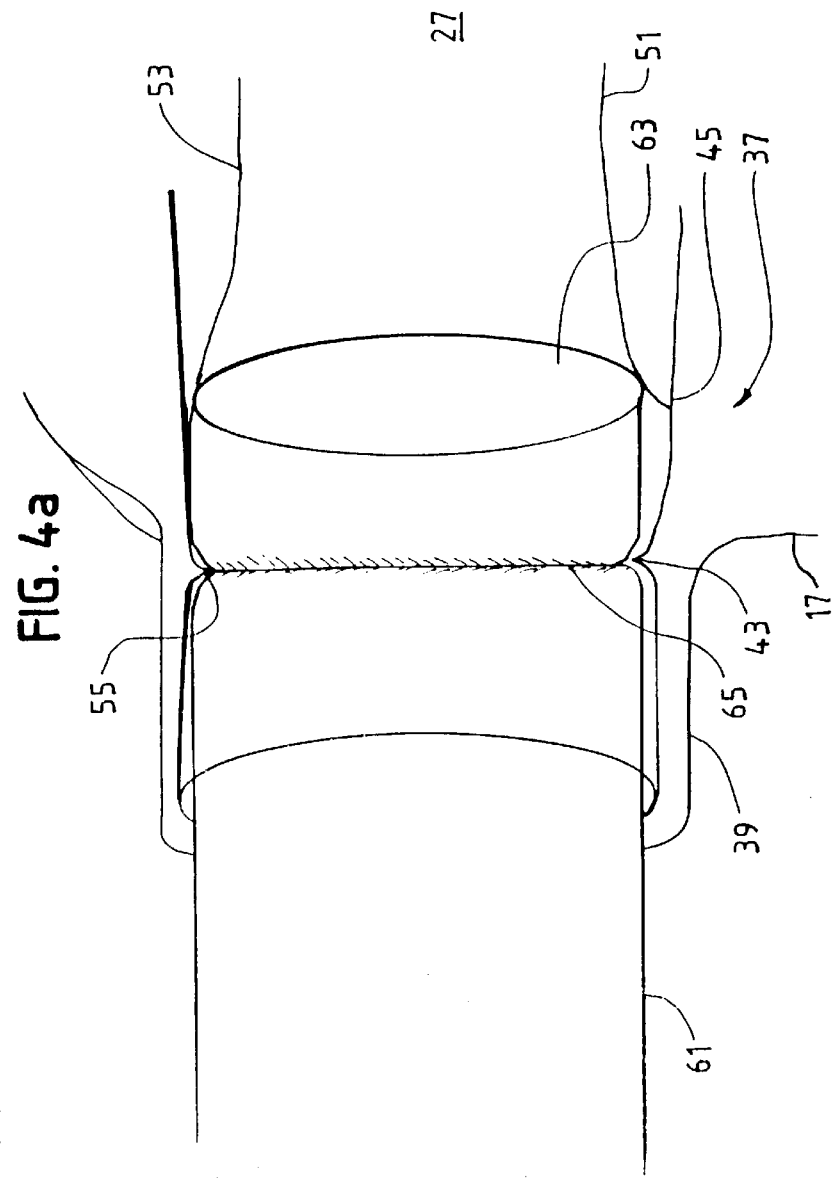

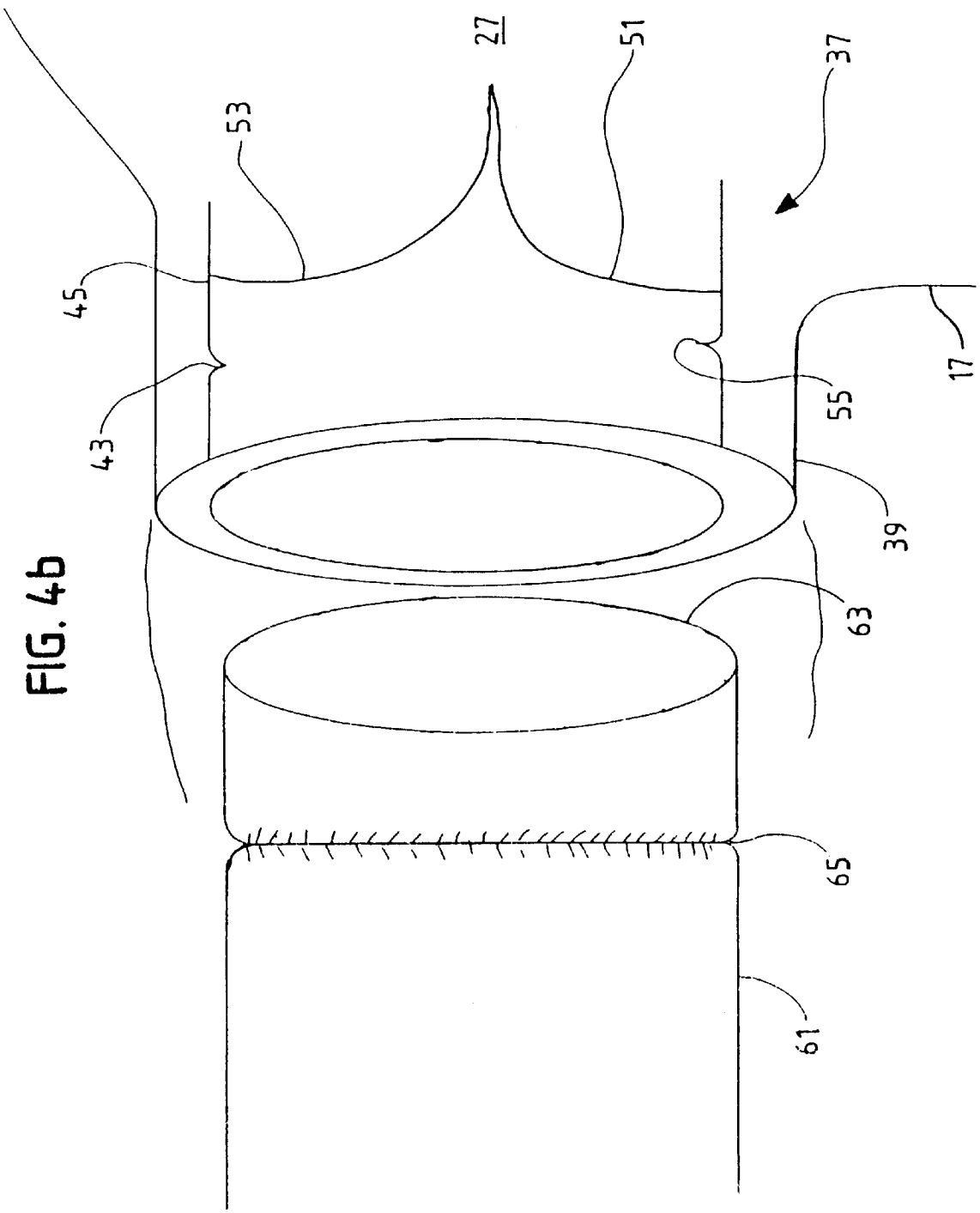

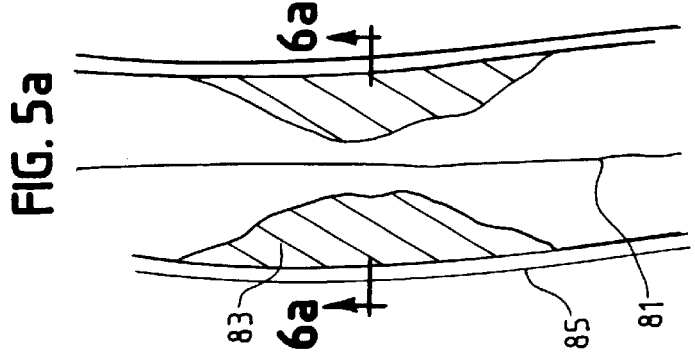
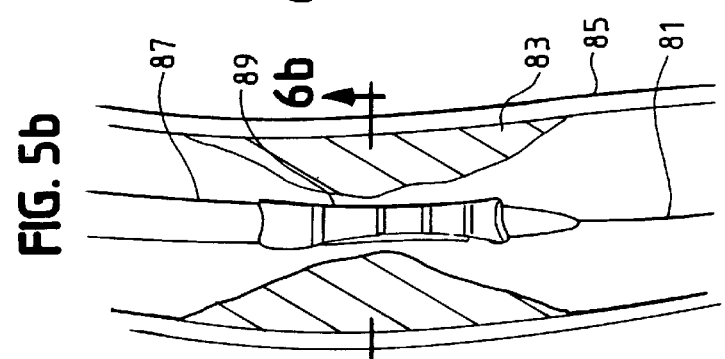
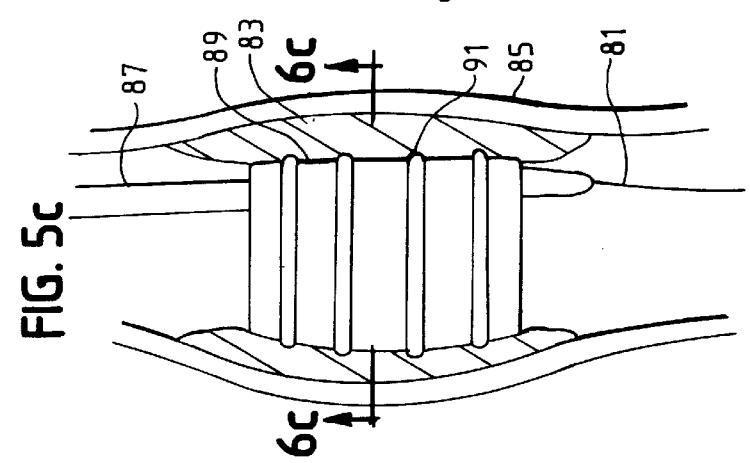
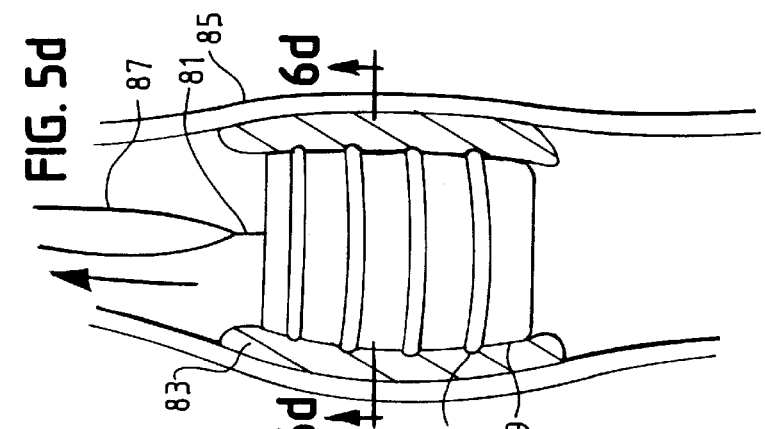
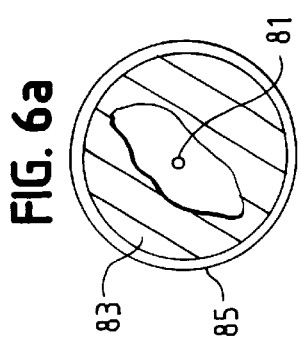
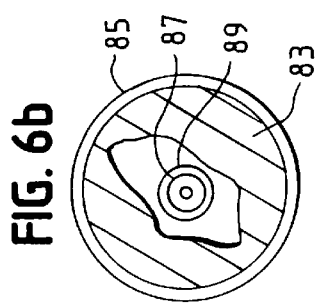
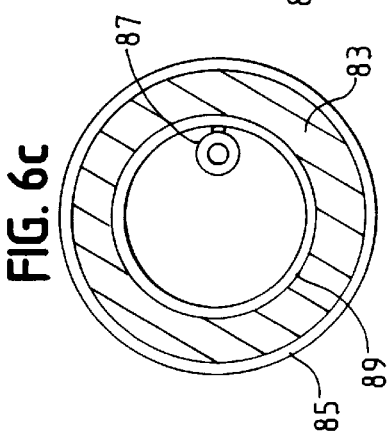
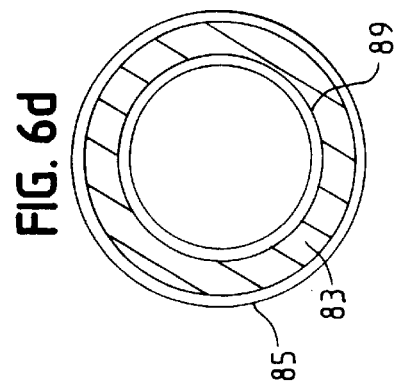

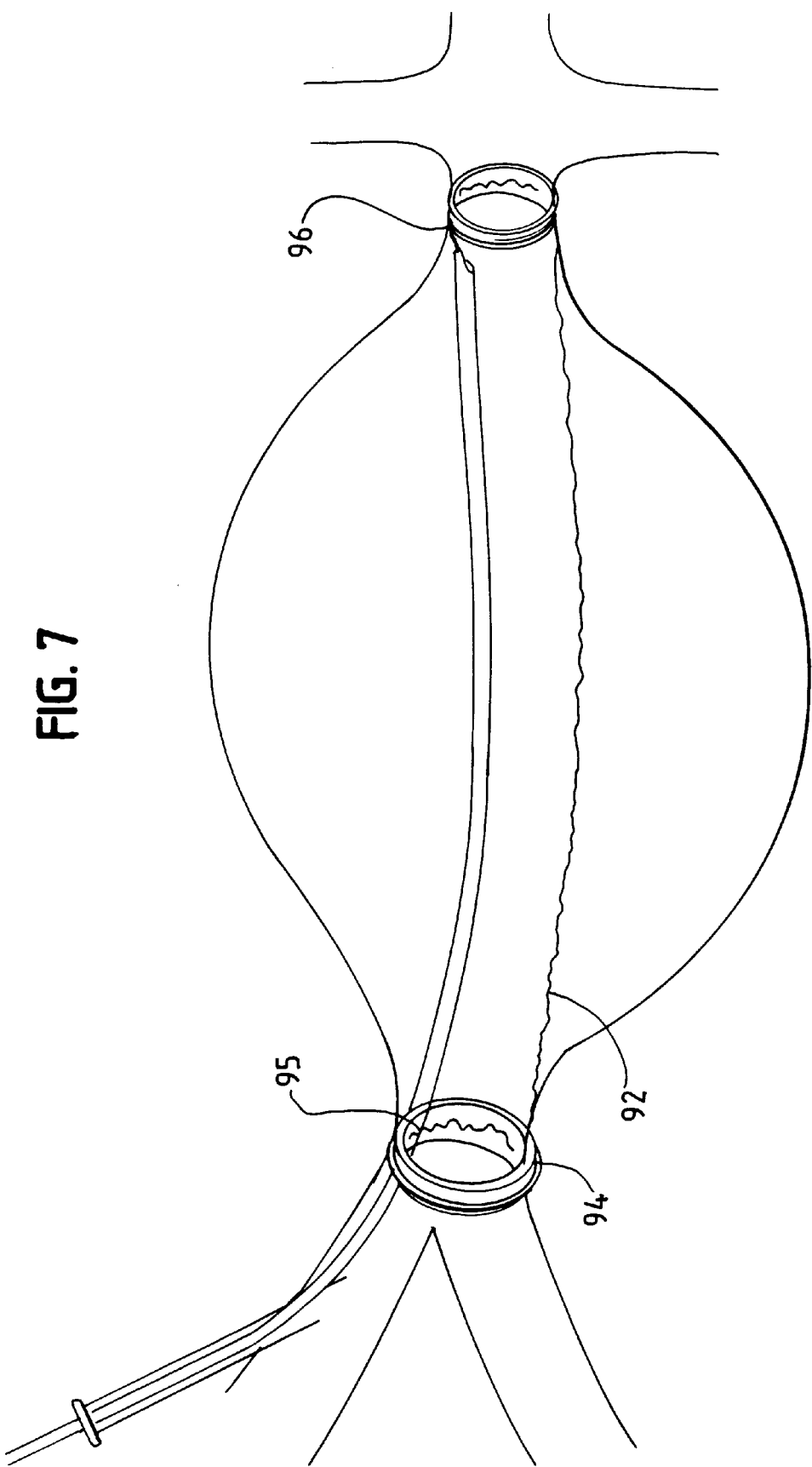

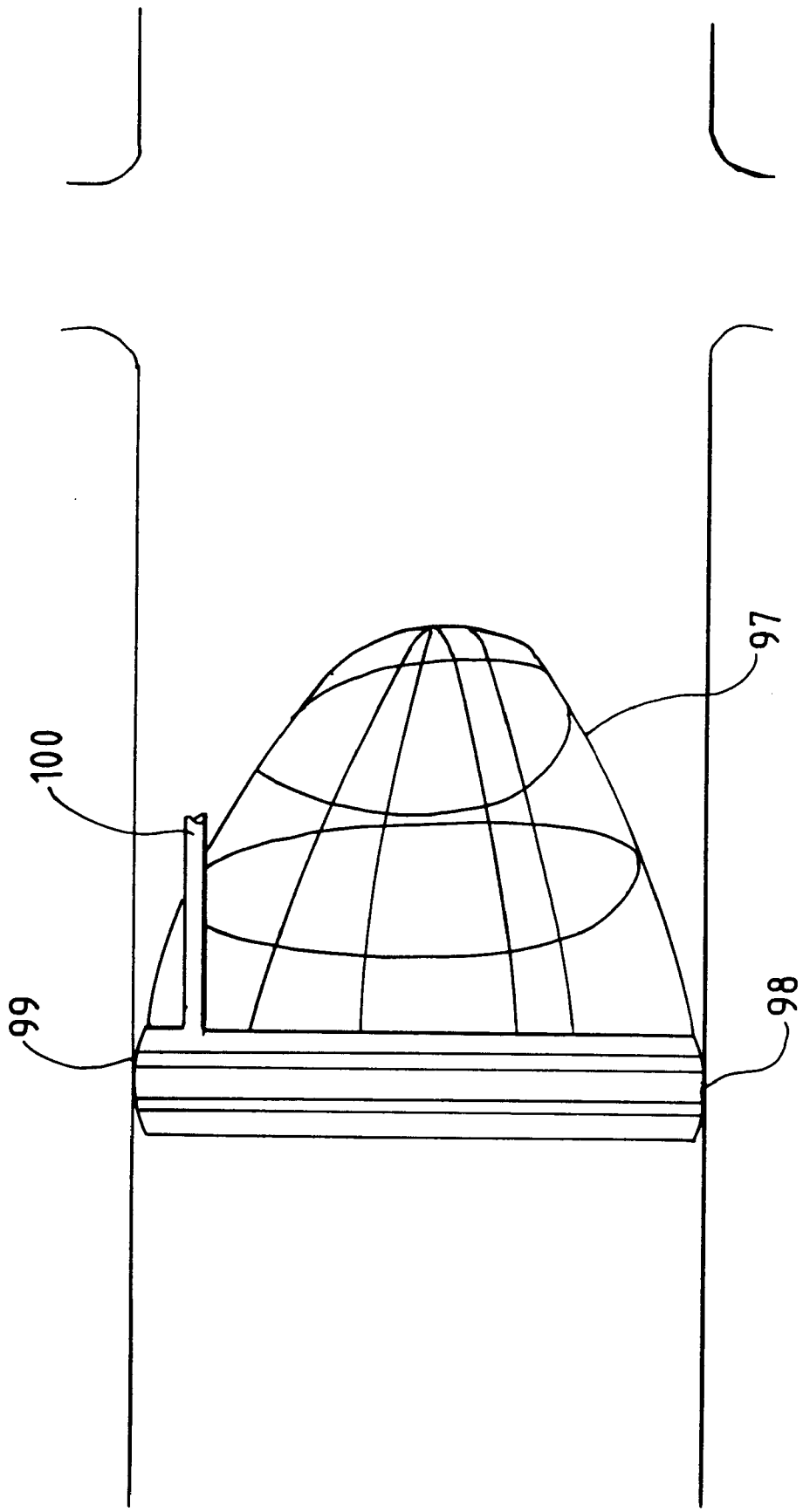

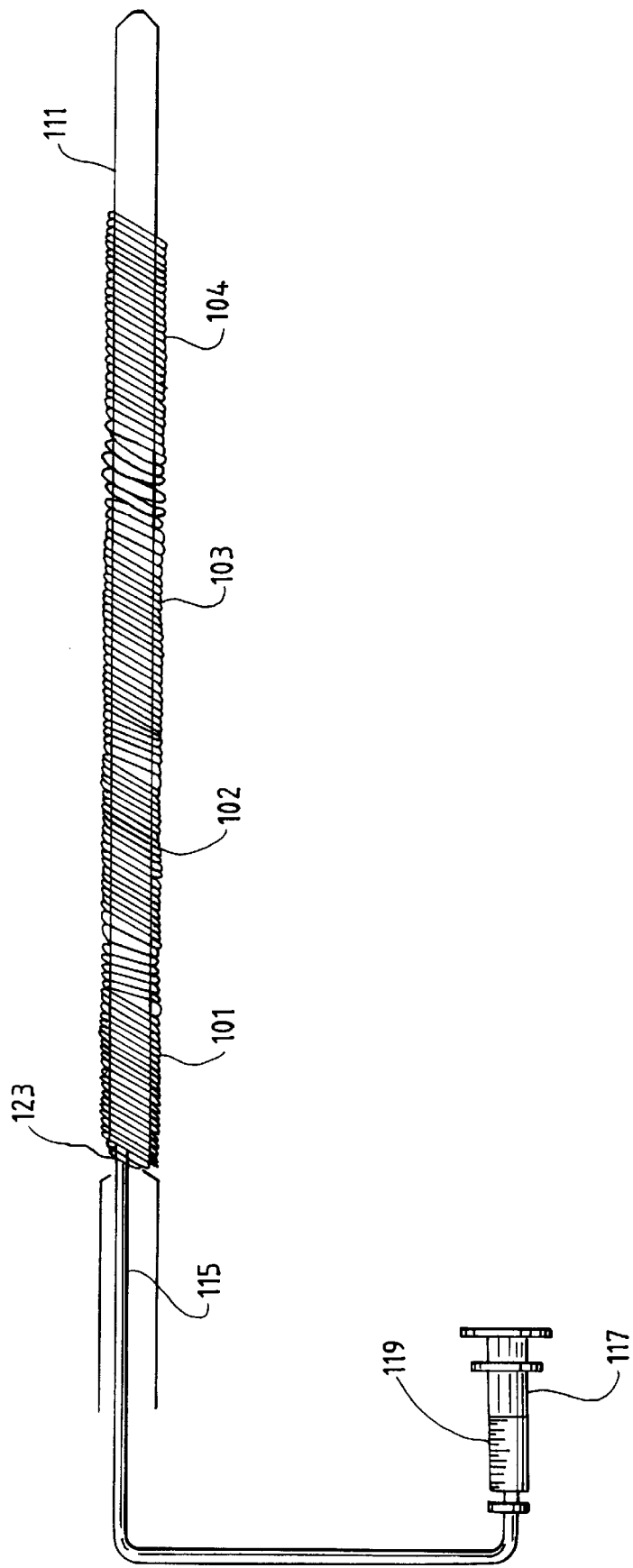

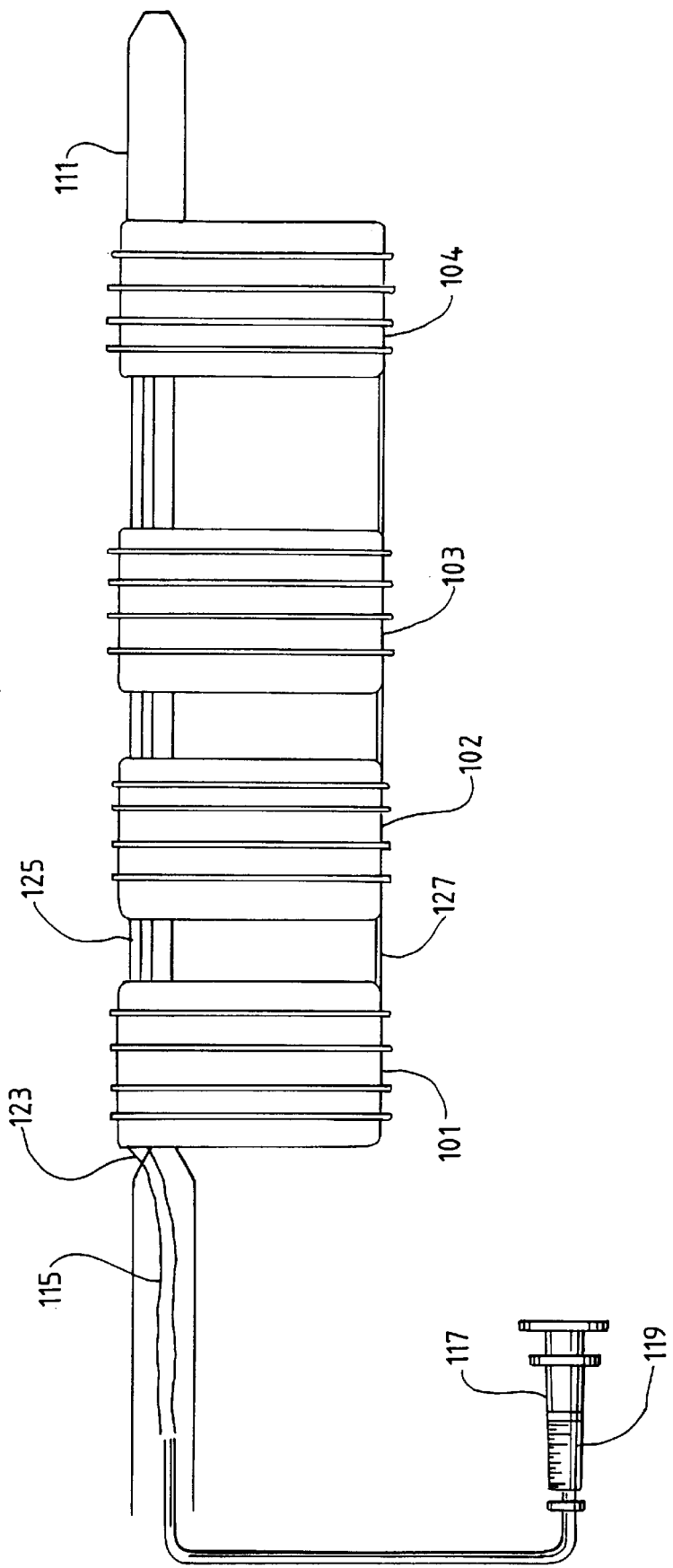

INFLATABLE INTRALUMINAL STENT AND METHOD FOR AFFIXING SAME WITHIN THE HUMAN BODY

BACKGROUND

Various tubular structures within the human body, such as the biliary duct system, excretory system and vascular system, may deteriorate so that medical repair is necessary. For example, weaknesses in the walls of the tubular structures or deteriorative diseases may affect the ability of the tubular structures to conduct fluids and, in turn, may be life threatening. Surgical and interventional radiological techniques have been a primary means of providing treatment for such problems. Such surgical and interventional radiological techniques involve inserting a catheter and other medical devices into the tubular structures through an incision in the patient's skin.

As an example, degenerative effects on blood vessels may cause a narrowing or constriction of the lumen of the vessel so that blood flow is restricted. Such a condition is known as "stenosis". Treatment of stenosis involves the use a stent to permanently widen the portion of the vessel that is obstructed.

The use of stents in the treatment of stenosis is well known. Stents are tubular bodies having a diameter which may be increased once they are properly positioned within the tubular structure. There are a variety of different stent designs, but by far most are made of metal wire or ribbon. The most widely used method of deploying a stent involves the use of a dilation catheter having an inflatable balloon at its distal end. The stent, its diameter at a minimum, is positioned over the uninflated balloon portion of the dilation catheter. With the aid of fluoroscopy, the physician then positions the catheter and stent at the proper location within the tubular structure. The balloon is then expanded which in turn expands the stent in a radial fashion so that the stent, now having an enlarged diameter, supports the wall of the tubular structure. Next, the balloon is deflated and the catheter is removed. By virtue of its deformable metal construction, the stent remains positioned in tension against, and in support of the tubular structure wail upon removal of the balloon and catheter.

Problems exist with such an arrangement, however, in that the irregular surfaces of most metallic stents are likely to damage the endothelial walls of healthy arteries during delivery. Furthermore, once the stent is positioned, repositioning is difficult if not impossible. To further complicate matters, misplacement of the stent can lead to catastrophic results such as the complete occlusion of the tubular structure. Finally, the stent may ultimately loose its tension against the wall and migrate to an undesired location.

Some stent designs feature anchoring pins, surgical staple-like clips or exposed barbs to secure the stent to the tube walls via penetration of the walls. Damage to the tubular wall may occur when a such device is being positioned within the tube. Furthermore, repositioning of such stents cannot be accomplished without damaging the tube walls.

Due to the above problems, extensive fluoroscopic examination is required to ensure the correct placement of existing stent designs to minimize the risk of misplacement and tissue damage.

Accordingly, it is an objective of the present invention to provide a stent, and a method of placing it, that allows for repositioning of the stent within a tubular structure of the body. It is also an object of the present invention to provide a stent, and a method of placing it, that allows for the stent to be affixed to the tubular structure inner walls in a manner that prevents both damage to the walls and migration of the stent after it has been affixed.

A further problem with existing stent designs is that they do not allow for the stent to be used to secure other medical devices to the tube walls. Many interventional radiology procedures require the insertion of medical devices, other than a stent, into the lumen of the tubular structures of a patient.

As an example, aneurysms may occur in blood vessels having weakened walls. An aneurysm is a ballooning of the wall of an artery. Left untreated, the aneurysm will frequently rupture resulting in a loss of blood through the rupture. Aneurysm repair involves inserting a vascular prosthesis, also known as a graft or stent-graft, into the lumen of the damaged vessel to reconstruct the section that is in need of repair. Such grafts must be anchored within the lumen of the blood vessel at the location of the aneurysm. The utility of a stent would be greatly increased if it could be used for such a purpose.

As such, it is also an object of the present invention to provide a stent that may be utilized to secure other medical devices to the inner walls of the tubular structure.

SUMMARY

The present invention is directed to an inflatable intraluminal stent and a method of among it to the interior surface of a tubular structure within the human body as a means of treating conditions such as stenosis. Intraluminal medical devices may also be attached to the inner surface of the stent. The stent of the present invention features an inflatable cuff having an inner surface, an outer surface, and an inlet and an outlet with a lumen extending therebetween. The outer surface has a friction-enhancing face that engages the interior surface of the tubular structure, without penetrating it, when the inflatable cuff is deployed.

If the initial placement of the stent within the tubular structure is not optimal, it may be deflated, repositioned to the optimal position and reinflated so as to again be affixed to the tubular walls via its outer surface. The tissue of the walls is not damaged or harmed by its exposure to the friction-enhancing face of the stent outer surface.

The stent is inflated with an inflation material that may contain a hardening agent. A valve, which is integral with the stent, allows it to be sealed in an inflated condition after it is placed in the proper position.

A number of the stents may be joined together so as to form a multi-ring stent. Such an arrangement may be used to affix medical devices which require more support due to their length or in situations requiring a stent of a length greater than the length of a single stent.

For a more complete understanding of the nature and scope of the invention, reference may now be had to the following detailed description of embodiments thereof taken in conjunction with the appended claims and accompanying drawings.

BRIEF DESCRIPTION OF THE DRAWINGS

FIG. 3 shows a perspective view of another embodiment of the stent of the present invention;

FIGS. 4a and 4b are enlarged partially broken away perspective views showing the detail of the mitre valve and breakaway valve connections of the stent of FIG. 1 in engaged and disengaged positions, respectively;

FIGS. 5a through 5d show in cross-section a constricted blood vessel with an elevational view of the stent of FIG. 1 being deployed therein in accordance with the method of the present invention;

FIGS. 6a through 6d show cross-sectional views corresponding to FIGS. 5a through 5b taken along line 2—2;

FIG. 7 shows a cross-sectional view of a blood vessel with an aneurysm and a stent-graft utilizing the stent of the present invention;

FIG. 8 shows a cross sectional view of an inferior vena cava with a filter disposed therein via the stent of the present invention;

FIGS. 9a through 9c show partial section, elevation and perspective views of another embodiment of the stent of the present invention, and the method of deploying the stent in accordance with the present invention, wherein multiple stents of the type of FIG. 1 are connected in a gang arrangement.

DESCRIPTION

Figure 1:
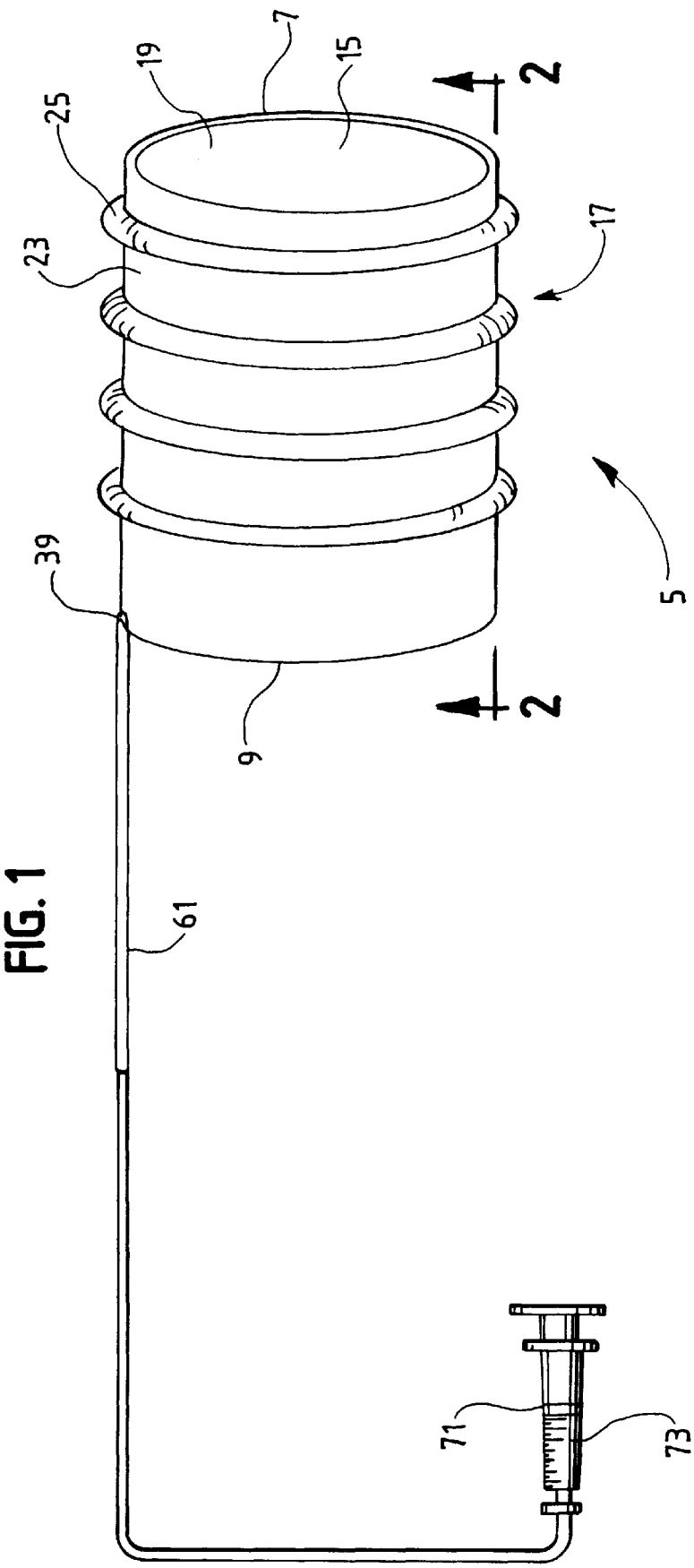
FIG. 1 shows a perspective view of an embodiment of the stent of the present invention.

Referring to FIG. 1, an embodiment of the inflatable intraluminal stent of the present invention is indicated generally at 5. The stent 5, shown in its inflated and deployed configuration, is a hollow cylinder and features an inlet 7, an outlet 9 and a lumen 15 extending between inlet 7 and outlet 9. The lumen of the stent is defined by an inflatable cuff, indicated generally at 17, having an inner surface 19 and an outer surface 23.

As shown in FIG. 1, outer surface 23 features a number of inflatable ridges 25 disposed about its circumference. While inflatable ridges are shown in the FIGS., any friction-enhancing outer surface, that would secure the inflated stent to the interior wall of a tubular structure without penetrating it, could be used. For example, the surface could feature nubs, bumps, indentations, etc.. As will be shown later, medical device may be secured to inner surface 19 of cuff 17 by way of biologically inert adhesives.

Inflatable cuff 17 is manufactured to the appropriate diameter and width to support or simulate the wall of, or to support a medical device within, the desired tubular structure of the patient. Inflatable cuff 17 is preferably constructed by extrusion and is drawn so as to have a low profile when viewed down the axis of the center of the ring defining cuff 17. Also, inflatable cuff 17 and its outer surface 23 are preferably composed of a polymeric plastic which is biologically inert. The material of cuff 17 must be able to withstand high inflation pressures and must be of sufficient durability to provide for decades of effective use within the body.

Figure 2:
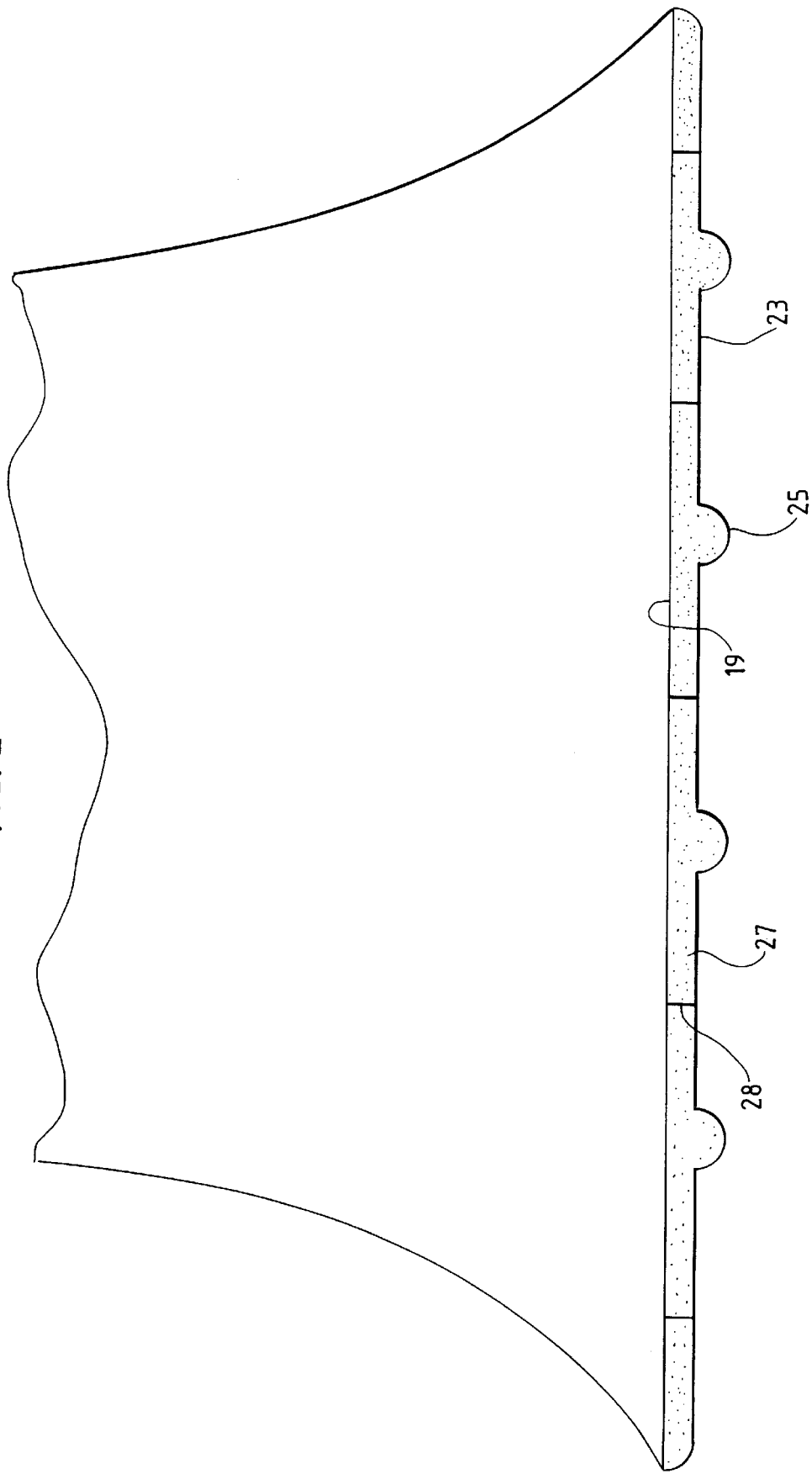
FIG. 2 shows a vertical sectional view of the stent of FIG. 1 taken along line 1—1.

As illustrated in FIG. 2, circumferential ridges 25 are in fluid communication with the inflatable chamber 27 of cuff 17. Spot welds 28, positioned incrementally about the circumference and parallel with the longitudinal axis of cuff 17, prevent distention of the flat portions of the outer surface 23 of cuff 17.

As an example of an alternative friction-enhancing surface, another embodiment of the stent of the invention is shown in FIG. 3. As illustrated in FIG. 3, the outer surface 30 of the cuff is made coarse by a combination of raised portions 31 and lowered portions 33. These surface features allow the inflated stent to grip the interior walls of a tubular structure with a force that is sufficient to prevent its migration.

In addition, it may be desirable in some applications to provide the cuff with an outer surface that promotes tissue ingrowth. This would allow the stent to become more integrated, and thus more firmly affixed, within the tubular structure as time progresses. Such a surface could be provided by combining a friction-enhancing surface, as discussed above, with a surface material such as TEFLON.

The cuff 17 is inflated and deflated by means of a valve, indicated generally at 37 in FIGS. 4a and 4b, which is integral with inflation port 39 of cuff 17. Preferably, valve 37 combines a breakaway valve 43 with a "duck bill" or "mitre" valve 45. Mitre valve 45 features opposing leaflets 51 and 53 which are constructed of a non-elastomeric, biologically inert material. Breakaway valve 43 features a circumferential rim 55 formed upon the interior surface of inflation port 39. Inflation tubing 61 features mating end 63 and circumferential notch 65. As shown in FIG. 4a, when inflation tubing 61 is in an engaged configuration with valve 37, mating end 63 separates opposing leaflets 51 and 53 so that cuff 17 may be inflated or deflated. When in this configuration, circumferential notch 65 engages circumferential rim 55 so as to secure inflation tubing 61 within inflation port 39.

Referring to FIG. 4b, once cuff 17 has been inflated (or deflated) to the desired level, a sharp tug on inflation tubing 61 in a direction away from inflation port 39 causes circumferential notch 65 and circumferential rim 55 to disengage. This allows easy withdrawal of mating end 63 from mitre valve 45 and inflation port 39. Upon withdrawal of the mating end 63 of inflation tubing 61, as shown in FIG. 3b, opposing leaflets 51 and 53 of mitre valve 45 close to seal the inflated cuff 17.

Referring back to FIG. 1, cuff 17 is inflated by way of an inflation syringe 71 with an inflation material 73. The inflation material could be a saline-based fluid or a material that contains a photo-activated or heat-activated hardening agent or any hardening agent that hardens over time. Typically, the inflation syringe 71 is mounted in a screw-feed pressure generating device provided with a manometer in order to accurately gauge inflation pressures. After cuff 17 has been installed and inflated, the material 73 hardens over time to permanently affix stent 5 within the tubular structure of the body via circumferential ridges 25.

FIGS. 5a through 5d, and corresponding FIGS. 6a through 6d, illustrate the steps to be performed in deploying the stent of the present invention in accordance with the method of the present invention. Referring to FIGS. 5a and 6a, a guide wire 81 is initially fed from outside of the patient's body, through an incision and finally, through the constricted portion 83 of a blood vessel 85.

Once guide wire 81 is in place, catheter 87, with stent 89 collapsed over it, is advanced along guide wire 81 so as to become positioned at the constricted portion 83 of blood vessel 85, as shown in FIGS. 5b and 6b. Inflation tubing, not shown in this view, is located within catheter 87 and is connected to stent 89 by the valve arrangement described in connection with FIGS. 4a and 4b. Stent 89 is then inflated using the technique described above. As shown in FIGS. 5c and 6c, stent 89 is inflated so that the size of the lumen of stent 89 approximates the lumen size of the original, unconstricted blood vessel. By doing so, constricted portion 83 is compressed between blood vessel wall 85 and stent 89, the latter of which is fixed in place by way of protruding ridges 91.

A unique feature of the present invention is its capability of being optimally positioned within a tubular structure in the body (in this case, a blood vessel) without causing damage to the surrounding tissue. Specifically, after stent 89 has been inflated so that ridges 91 affix the stent to the tubular walls without penetration, the position of the stent is examined fluoroscopically to determine if it is optimal. If not, stent 89 may be deflated, repositioned and then reinflated. It is important to note that the tissue of the vessel walls is not damaged by exposure to ridges 91 of the stent.

As the final step of the procedure, as shown in FIGS. 5d and 6d, catheter 87 is removed from stent 89 so that the former may be removed from the blood vessel. As discussed in reference to FIGS. 4a and 4b, breakaway and mitre valves allow the inflation tubing within catheter 87 to be removed from the stent so that the stent may be sealed in an inflated condition. Finally, guidewire 81 is removed from the blood vessel.

Note that utilization of the stent and method of the present invention for the treatment of stenosis is presented only as an example of its potential applications. A non-exhaustive list of other applications includes: placing filters in the inferior vena cava, use of the stent in the vascular or biliary system to maintain the patency of the respective tubular structures and endoarterial grafts via a percutaneous approach. In order to accommodate some of these applications, as stated earlier, an intraluminal medical device may be attached to the interior surface of the stent of the present invention.

As an illustration, FIG. 7 shows a stent-graft utilizing the stent of the present invention to treat an aneurysm. A graft 92 is held by its end portions to the interior surfaces of stents 94, shown in an inflated condition, by biologically inert adhesive 95. The stent-graft is secured to the vessel walls via ridges 96 so that blood passes through graft 92.

As another example, FIG. 8 shows a filter 97 disposed within the inferior vena cava via the stent of the present invention. Filter 97 is attached to the interior surface of stent 98. Stent 98, shown in an inflated condition, is held within the inferior vena cava by ridges 99. In some applications, it may be desirable to temporarily place filter 98 in the inferior vena cave The stent of the present invention is perfectly suited to such an application in that it can be deflated for retrieval without damaging the interior walls of the inferior vena cava. In such instances, stent 98 is inflated with a saline-based material that does not contain a hardening agent. This allows for easy deflation of stent 98 for retrieval. During the retrieval process, stent 98 is deflated and the inflation stalk 100 is snared with a separate device. The stent and attached filter may then removed from the inferior vena cava.

Figure 9C:
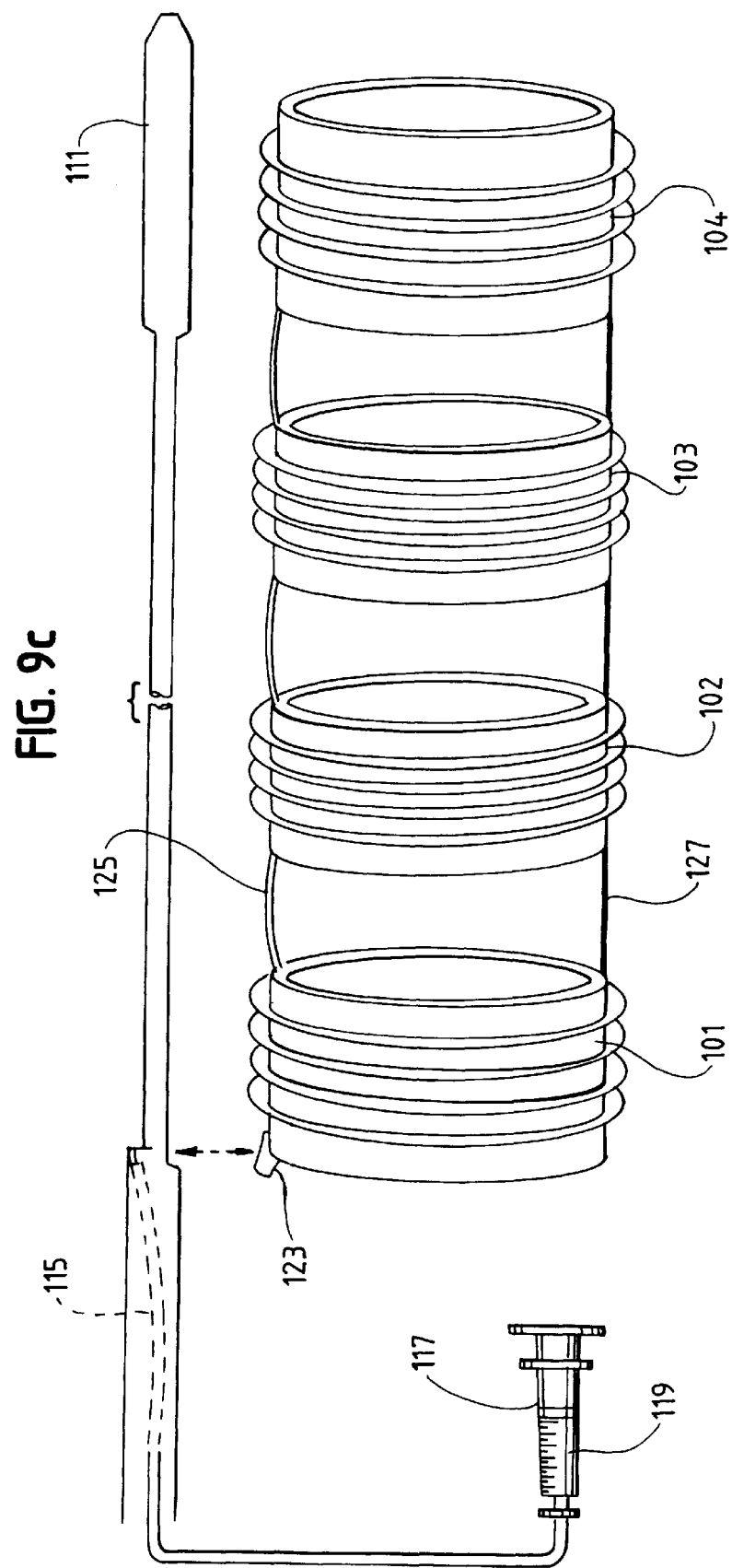

Referring to FIGS. 9a through 9c, a ganged arrangement of four inflatable stents, 101 through 104, is shown. Each of the stents is similar in construction to stent 5 of FIG. 1. Such an arrangement preferably is used to affix medical devices which require more support due to their length, such as long tubes or endo-arterial grafts. Alternatively, the ganged arrangement may be utilized in situations requiring a stent of a length greater than the length a single cuff. Examples include colonic or esophageal stents. FIGS. 9a through 9c also show how such a ganged arrangement may be deployed in accordance with the method of the present invention.

FIG. 9a shows the multi-ring stent collapsed over deployment catheter 111. FIG. 9a also illustrates that, via a partial sectional view of catheter 111, inflation tubing 115 is located within catheter 111 and connected at one end to stent 101 via port 123. Stent 101 features breakaway and mitre valves (not shown) of the type illustrated in FIGS. 4a and 4b within its port 123. As will be shown below, stents 101 through 104 are in fluid communication with one another. The opposing end of inflation tubing 115 is connected to inflation syringe 117 which is filled with inflation material 119.

FIG. 9b illustrates the multi-ring stent in an inflated condition, such as would be desired once the stent is properly positioned within the tubular structure of a patient. Connecting inflation tubing 125 interconnects stents 101 through 104 so that all four stents can be simultaneously inflated. The inflation tubing 125 and stents 101 through 104 are formed into an integral construction by fastening the stents to the inflation tubing, the latter of which is initially provided with apertures (not shown) for conveying fluid into the cuffs. Fastening may be performed using a biologically inert adhesive, thermal welding or any other suitable fastening method. In the configuration shown in FIG. 9b, inflation material 119 has been injected into stents 101 through 104 by manipulation of inflation syringe 117. Stents 101 through 104 are also secured together by stabilizing bridging wire 127 so as the enhance the integrity of the multi-ring stent. Note that tape may be used in place of wire 127.

FIG. 9c shows the inflated multi-ring stent after catheter 111 has been pulled away so that catheter 111 may be removed from the tubular structure of the patient. As the catheter is pulled away, the breakaway valve within port 123 releases inflation tubing 115 and the mitre valve seals port 123 in a manner similar to the one illustrated in FIG. 4b. As a result, inflation material 119 cannot escape from the multi-ring stent.

The present invention can be constructed in many different sizes and shapes. The only criterion which must be met is that the stent must be of an appropriate width and diameter so that the tubular wall may be simulated or supported by the stent or the medical device to be used can be fully supported within the tubular structure by the stent. Not only can the invention be practiced in small structures such as the vascular system, but also, the stent may be affixed within much larger structures such as the excretory system.

While the preferred embodiments of the invention have been shown and described, it will be apparent to those skilled in the art that changes and modifications may be made therein without departing from the spirit of the invention, the scope of which is defined by the appended claims.

What is claimed is:

1. An inflatable intraluminal stent adapted to be secured to the interior of a tubular structure within the human body comprising:

a) an inflatable and deflatable cuff of generally hollow cylindrical continuation having a collapsible lumen, an inner surface, an inlet, an outlet and a friction enhancing outer surface, said friction-enhancing outer surface featuring inflatable protrusion(s) including at least one circumferential ridge disposed about the inflatable cuff, said friction-enhancing outer surface engaging the interior of the tubular structure without penetration to prevent the cuff from moving in a longitudinal direction with respect to the tubular structure when said cuff is in a fully inflated condition;

b) means for injecting an inflation material into said cuff to inflate it; and c) a valve integral with the inflatable cuff for permitting entry of the inflation material from the means for injecting and thereafter sealing said cuff to prevent deflation.

2. The inflatable intraluminal stent of claim 1 wherein the friction-enhancing outer surface is a coarse surface.

3. The inflatable intraluminal stent of claim 1 further comprising a plurality of spot welds between the inner surface and the friction-enhancing outer surface of the inflatable cuff in staggered relationship with the inflatable protrusion(s) to limit distention between the inner surface and the friction-enhancing outer surface.

4. The inflatable intraluminal stent of claim 1 wherein the friction-enhancing outer surface is constructed of a material that promotes tissue ingrowth.

5. The inflatable intraluminal stent of claim 4 wherein the material that promotes tissue ingrowth is TEFLON.

6. The inflatable intraluminal stent of claim 1 wherein the inflatable cuff is composed of a polymeric plastic which is biologically inert.

7. The inflatable intraluminal stent of claim 1 wherein the inflation material includes a hardening agent.

8. The inflatable intraluminal stent of claim 1 wherein the valve is a mitre valve.

9. The inflatable intraluminal stent of claim 1 wherein the valve is of a breakaway design to permit separation from the means for injecting.

10. The inflatable intraluminal stent of claim 1 further comprising means for securing an intraluminal medical device to the inner surface of the inflatable cuff.

11. The inflatable intraluminal stent of claim 10 wherein the intraluminal medical device is a graft for repairing aneurysms.

12. The inflatable intraluminal stent of claim 10 wherein the intraluminal medical device is a vena cava filter.

13. The inflatable intraluminal stent of claim 1 wherein the means for injecting an inflation material into said inflatable cuff to inflate it includes an inflation syringe and inflation tubing.

14. An apparatus for disposition within the lumen of a tubular structure within the human body comprising:
   a) a cuff having a collapsible lumen, an inner surface and a friction-enhancing outer surface with an inflatable and deflatable chamber disposed therebetween, the cuff also having an inflation port in fluid communication with the inflatable chamber,
   b) said friction-enhancing outer surface featuring inflatable protrusion(s) including at least one circumferential ridge disposed about the inflatable cuff and affixing the cuff with the lumen of the tubular structure without penetration of the tubular structure when the cuff is fully inflated so that movement of the cuff in a longitudinal direction with respect to the tubular structure is prevented;
   c) means for inflating the cuff with inflation material in fluid communication with said inflation port; and
   d) a valve integral with sad inflation port for permitting entry of the inflation material from the means for inflating and thereafter sealing said cuff to prevent deflation.

15. The apparatus of claim 14 wherein the friction-enhancing outer surface is a coarse surface.

16. The inflatable intraluminal stent of claim 14 wherein the friction-enhancing outer surface is constructed of a material that promotes tissue ingrowth.

17. The inflatable intraluminal stent of claim 10 wherein the material that promotes tissue ingrowth is TEFLON.

18. The apparatus of claim 14 wherein the valve is a mitre valve.

19. The apparatus of claim 14 wherein the valve is of a breakaway design to permit separation from the means for inflating.

20. The apparatus of claim 14 further comprising means for securing an intraluminal medical device to the inner surface of the cuff.

21. The inflatable intraluminal stent of claim 20 wherein the intraluminal medical device is a graft for repairing aneurysms.

22. The inflatable intraluminal stent of claim 20 wherein the intraluminal medical device is a vena cava filter.

23. An apparatus for disposition within the lumen of a tubular structure within the lumen body comprising:
   a) a plurality of cuffs, each of said plurality of cuffs having an inner surface and a friction enhancing outer surface with an inflatable chamber disposed therebetween, the inflatable chambers of said plurality of cuffs being in fluid communication with one another;
   b) said friction-enhancing outer surfaces featuring inflatable protrusion(s including at least one circumferential ridge disposed about the inflatable cuff and affixing the plurality of cuffs within the lumen of the tubular structure without penetration of the tubular structure when the plurality of cuffs are inflated;
   c) means for inflating the plurality of cuffs with inflation material; and
   d) a valve integral with one of the plurality of cuffs for permitting entry of the inflation material from the means for inflating and thereafter sealing said cuff to prevent deflation.

24. The apparatus of claim 22 further comprising means for securing an intraluminal medical device to the inner surfaces of the cuffs.

* * * * *